United States Patent [19]

Nara et al.

[11] Patent Number: 4,639,220
[45] Date of Patent: Jan. 27, 1987

[54] APPARATUS FOR DETERMINING THE THREE-DIMENSIONAL POSITION AND ATTITUDE

[75] Inventors: Toshio Nara, Odawara; Sumiya Hobo, Tokyo; Masao Kashiwada, Ebina; Motoyuki Totsuka, Atsugi; Takao Hoshiai, Tokyo; Katsutoshi Umetani, Hiratsuka; Keisuke Akamatsu, Isehara; Tomohide Inada, Yamato; Hisao Takayama, Tokyo, all of Japan

[73] Assignee: Nippon Avionics Co., Ltd., Tokyo, Japan

[21] Appl. No.: 555,976

[22] Filed: Nov. 29, 1983

[30] Foreign Application Priority Data

Nov. 29, 1982 [JP] Japan ............................ 57-209077

[51] Int. Cl.$^4$ .............................................. A61C 19/04
[52] U.S. Cl. ......................................... 433/69; 433/73; 433/68
[58] Field of Search ............................ 433/69, 73, 68

[56] References Cited

U.S. PATENT DOCUMENTS

| 1,786,915 | 12/1930 | McLean | 433/68 |
| 2,794,253 | 6/1957 | Fitzsimmons | 433/69 |
| 2,814,876 | 12/1957 | Stuart | 433/69 |
| 3,052,030 | 9/1962 | Spence | 433/73 |
| 3,350,782 | 11/1967 | Guichet | 433/73 |
| 3,431,649 | 3/1969 | Guichet | 433/73 |
| 3,905,112 | 9/1975 | Swanson | 433/73 |
| 4,084,319 | 4/1978 | Dragan | 433/73 |
| 4,096,637 | 6/1978 | Stade | 433/73 |
| 4,292,026 | 9/1981 | Yokota | 433/69 |

FOREIGN PATENT DOCUMENTS

| 2825204 | 12/1979 | Fed. Rep. of Germany | 433/69 |
| 2832838 | 2/1980 | Fed. Rep. of Germany | 433/69 |

Primary Examiner—Robert Peshock
Assistant Examiner—J. Hakomaki
Attorney, Agent, or Firm—Oblon, Fisher, Spivak, McClelland, & Maier

[57] ABSTRACT

An apparatus for measuring the three-dimensional position and attitude of upper and lower clutches attached on patient's maxillary and mandibular teeth for computerized measurement of the mandibular movements necessary for the fabrication of dental prostheses is disclosed. The apparatus includes a part of a sphere that is fixed to the mandible and which is marked with a reference line and a part of another sphere of substantially the same radius as that of the above sphere, which is fixed to the maxilla and which is also marked with a reference line. The surfaces of the two spheres are caused to slide against each other, with their centers being in alignment, thereby achieving the measurement of the relative attitude of the two spheres.

2 Claims, 10 Drawing Figures

APPARATUS FOR DETERMINING THE THREE-DIMENSIONAL POSITION AND ATTITUDE

FIELD OF THE INVENTION

The present invention relates to an apparatus for determining the three-dimensional position and attitude. More particularly, the invention relates to an apparatus for determining the three-dimensional position and attitude, such as skew, of upper and lower clutches mounted on the patient's teeth during computer measurements of the mandibular movements necessary for reconstructive dentistry.

BACKGROUND OF THE INVENTION

Reconstructive dentistry involves the checking of the occlusion of maxilla and mandible of the patient as well as the making of prostheses such as crowns, bridges and partial or full dentures. In this field of dentistry, measurements of the mandibular movements constitute an important stage of diagnosis and the proper adjustment of an articulator for each patient. However, in the absence of a simple method and apparatus for the accurate measurements of the mandibular movements, the dentist has to resort to a trial-and-error approach either by taking interocclusal record or tracing the three-dimensional locus of various points on the mandible with the aid of a pantograph. In the former method, the record is placed on a semi-adjustable articulator which is manipulated to obtain optimum fitting to the record. In the latter method, the trace is transferred to a fully adjustable articulator which is manipulated to obtain a faithful reproduction of the trace. These methods are lengthy and involve the dentist's experience and skill to avoid erroneous measurements. Therefor, they are not best suited to clinical purposes and are often omitted from the practice of reconstructive dentistry. However, the fact remains that dental practice must be based on the accurate measurements of the mandibular movements. Prostheses made without meeting this requirement fail to achieve the satisfactory mastication. Furthermore, defective prostheses may induce arthritis of the temporomandibular joint which is sometimes complicated with neurosis. The need for an early solution to these problems is increased as the preference of people for foods is diversified and their mean life is extended.

The inventors previously proposed a method and apparatus that provided the simple and accurate measurement of the mandibular movements by simply detecting the three-dimensional displacement of a certain point fixed to the front side of the anterior teeth in the mandible. The proposed apparatus includes a device which, while the mandible is moved under limited conditions, detects the three-dimensional displacement of specific point on the front side of the mandible and outputs the detected displacement information, and a memory that stores this displacement information and the data of the measurements of the size of the face including the mandible. The necessary data of the mandibular movement is obtained by performing operations on the three-dimensional displacement information for the specific point and the measured data of the facial size. Alternatively, the specific type of the mandibular movements is determined by making comparison with known data for the mandibular movements. Details of this technique are given in Japanese Patent Application (OPI) No. 163043/80 (the symbol OPI as used herein means an unexamined Japanese patent application) filed by the present inventors under the title "Apparatus for electronic measurements of the mandibular movements" and in Japanese Patent Application No. 80316/81 also filed by the same inventors under the title "Method and apparatus for determining the type of mandibular movements". An example of the "device which detects the three-dimensional displacement of a specific point on the front size of the mandible and outputs the detected displacement information" is the following: a point light source is mounted on the front end of the mandible of the patient; three units of one-dimensional light image detector are arranged in orthogonal directions in a fixed manner with respect to the maxilla and in proximity around said point light source; the position of said point light source is read by said three detectors in terms of one-dimensional light image signals in orthogonal directions and these signals are subsequently converted to three-dimensional displacement signals for the specific point at the front end of the mandible. A specific example of this appearance is shown in Japanese Patent Application (OPI) No. 116258/79 also filed by the present inventors.

OBJECTS OF THE INVENTION

Therefore, one object of the present invention is to provide an apparatus for measuring the three-dimensional position and attitude of a rigid body in the fixed reference coordinate system.

Another and more specific object of the invention is to provide an apparatus that ensures a simple and precise determination of the three-dimensional position and attitude of the upper and lower clutches, used in reconstructive dentistry, with respect to the reference plane set on the maxilla. The obtained three-dimensional information is used for electronic measurement of the mandibular movements.

SUMMARY OF THE INVENTION

The above objects of the invention can be achieved by an apparatus comprising a spherical inner part of a gyroscope-like structure adapted to be fixed to the object, said inner part consisting of segments, an outer ring of said gyroscope-like structure which is fixed to a fixed reference coordinate system and which is touched internally by said spherical inner part of said gyroscope-like structure, said inner part of said gyroscope-like structure being marked with three lines of longitude and being slideable relative to said outer ring having three scales thereon, said three scales on the outer ring being disposed on its surface so as to be indicated by said three lines of longitude on said inner part, thereby enabling the user to calculate the three-dimensional attitude of the object in terms of three Euler's angles from readings of said three scales on the outer ring indicated by said three lines of longitude on said inner part.

The preferred embodiments of the present invention are hereunder described by reference to the accompanying drawings.

DETAILED DESCRIPTION OF THE PREFERRED EMBODIMENTS

Figure 1:
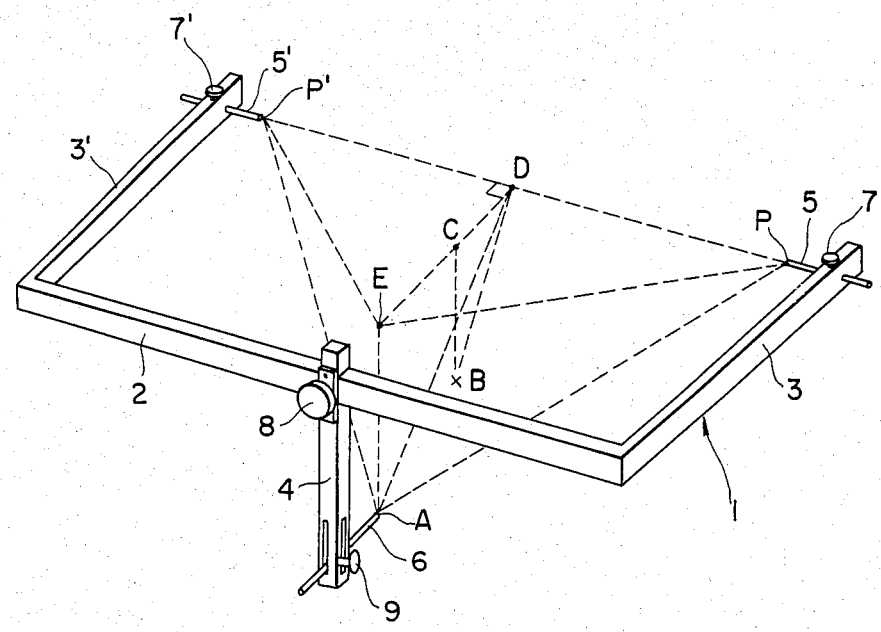
FIG. 1 is a perspective view of a common caliper for measuring various dimensions of a human face.

As mentioned before, the techniques described in Japanese Patent Application (OPI) No. 163043/80 and Japanese Patent Application No. 80316/81 involve the measurement of facial size, the results of which are used for the calculation of the mandibular movements or for comparison with known data of the mandibular movements. The method of obtaining the data of facial size is hereunder described by reference to FIG. 1. Triangle PAP' is generally referred to as the mandibular triangle and is formed by connecting the centric points P and P' of the right and left condyles of the mandible and incisal point A which is the midpoint of the two frontmost teeth in the mandible. Suppose this triangle PAP' is in the position assumed by a patient whose mouth is closed. In FIG. 1, D is the intersection of the axis P-P' with a line drawn perpendicularly to that axis, and E is the intersection of a plane parallel to the occlusal plane (or the Frankfort plane), which becomes substantially horizontal when the patient faces to the front, with a line drawn perpendicularly to that plane (which is hereunder referred to as the horizontal plane).

In the actual measurement of the mandibular movements, the constancy of the measuring conditions is important. For this purpose, a pair of tools called clutches are fixed by plaster of Paris to the teeth in the upper and lower jaws, and the proper occlusion of the two clutches is attained by sliding a pin projecting from the lower clutch to contact the underside of the upper clutch. If B is written for the tip of this pin, C is the intersection of the horizontal plane with a line drawn vertically to this plane.

Indicated generally at 1 in FIG. 1 is a face-bow which consists of a transverse beam 2, arms 3 and 3' connected perpendicularly to this beam and included in the same plane, and a single leg 4 which is also connected to the transverse beam 2 and is perpendicular to the plane defined by the transverse beam 2 and the arms 3,3'. The free ends of the arms 3, 3' and the leg 4 are provided with pointers 5, 5' and 6, respectively. The pointers 5, 5' are so designed that they can be extended or retracted in the plane defined by the transverse beam 2 and the arms 3, 3' and in the direction vertical to the arms 3,3'. The pointers 5, 5' are fixed by clamps 7, 7', respectively, at the positions where their tips contact the centers of the two condyles P, P'. The pointers 5, 5' are each provided with a calibrated scale as an aid to determine the length of line P-P' which is generally referred to as the intercondylar distance. The leg 4 is in the midpoint of the transverse beam 2. It can be moved horizontally along the length of the beam and fixed in position by a clamp 8. The pointer 6 is so designed that it can be extended or retracted in a plane parallel to the plane defined by the transverse beam 2 and the arms 3, 3' and in the direction perpendicular to the leg 4. The pointer 6 is also movable vertically relative to the leg 4. The pointer 6 can be fixed in position by a clamp 9.

The lengths of lines P-D, P'-D, A-E and ED can be determined by the following procedure. First, the plane defined by the transverse beam 2 and the arms 3, 3' is made parallel to the horizontal plane. Then, the horizontal position of the leg 4 as well as the two-dimensional position (including the vertical position and that in the direction normal to the leg 4) of the pointer 6 are adjusted so that the tip of the pointer 6 contacts point A of the mandibular triangle. Then, the leg 4 and the pointer 6 are fixed in position by the clamps 8 and 9. The length of the line P-D can be determined by reading the horizontal position of leg 4 on a scale marked on the transverse beam 2.

Given the length of the line P-D, the length of the line P'-D can be calculated by subtracting the length of the line P-D from the length of the line P-P'. The length of the line A-E can be determined by reading the vertical position of the pointer 6 on a scale marked on the leg 4. If the pointer 6 is also marked with a calibrated scale, the length of the line E-D can be determined by reading the position of the pointer 6 in the direction normal to the leg 4. The length of the line C-D can be determined by a similar method.

These are the procedures employed for obtaining data of facial size including the lengths of the P-P', P-D, P'-D, A-E, E-D, and C-D that are used for calculation of the mandibular movements or comparison with known data on mandibular movements. As a result, the three-dimensional position of point A with respect to the reference plane of the maxilla can be determined.

Figure 2:
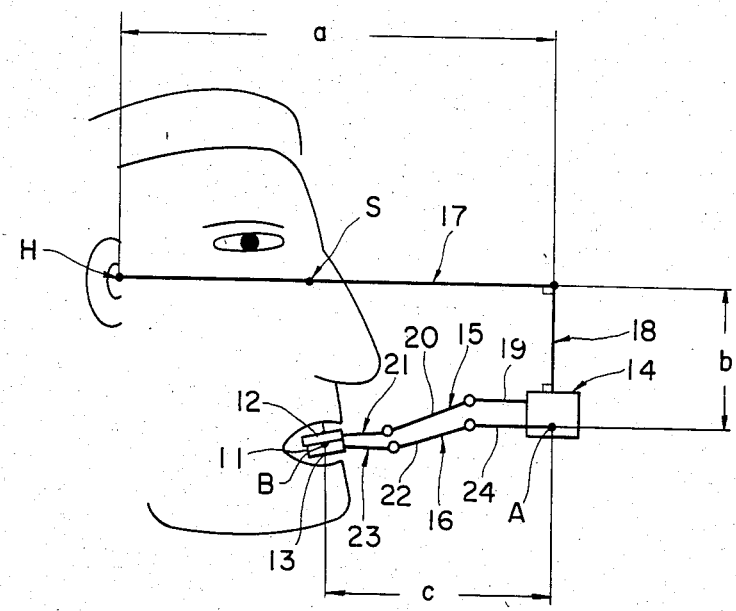
FIG. 2 shows schematically the conventional method for measuring various dimensions of a human face.

In the actual measurement of the mandibular movements, however, a pair of clutches consisting of a lower clutch 11 and an upper clutch 12 (see FIG. 2) are fixed to the teeth of the maxilla and mandible by plaster of Paris and the proper occlusion of the two jaws is established by sliding a pin 13 which projects from the lower clutch 11 to contact the underside of the upper clutch 12. In FIG. 2, the tip of the pin 13 that contacts the upper clutch 12 is indicated at B. A sensor 14 comprising three units of a one-dimensional light image detector positioned in orthogonal directions is fixed to the upper clutch 12, whereas a point light source is fixed as point A to the lower clutch 11. The three-dimensional displacement of the point A can be measured by the sensor 14.

However, the positions of the two clutches 11, 12 as well as their posture including their skew (or inclination) differ from one patient to another depending not only on the teeth in their maxilla and mandible but also on the way the clutches 11, 12 are mounted on the jaws. These factors influence the results of calculation of the mandibular movements and must be precisely determined before calculation the mandibular movements.

Conventionally, the sensor 14 and point light source A are placed in a fixed position with respect to some reference plane for the maxilla (maxillary reference plane), and the sensor 14 and the upper clutch 12 are connected by a universal ball joint 15, whereas the point light source A is connected to the lower clutch 11 by another universal ball joint 16. The relative position and inclination of the upper clutch 12 with respect to the sensor 14 are measured by a scale and a protractor, respectively. However, the three-dimensional measurement of these parameters is very difficult to make in dental practice without causing errors. The measurement of the position and attitude of the lower clutch 11 is unnecessary because it is fixed to the mandibular teeth with the aid of a setup tool that enables the fixing of the lower clutch 11 together with the upper clutch 12.

As further disadvantages, the universal ball joints 15 and 16 require the use of many fasteners (typically screws), while often failing to ensure positive fixing of the sensor 14 and the point light source A. To avoid these problems, the sensor 14 and the point light source A are usually placed on a fixed position with respect to the upper and lower clutches 11 and 12 rather than with respect to the maxillary reference plane. According to this improved technique, the position and attitude of the sensor 14 and the point light source A vary together with the upper and lower clutches 11, 12 so the parameters that need measurement are only the three-dimensional position and attitude of the two jaws. Thus, there is no need for measuring the facial dimensions with respect to the sensor 14 and point light source A as shown in FIG. 2.

First, the conventional method for obtaining data on facial dimensions is briefly described by reference to FIG. 2. The parameters to be measured are the position of the point light source A connected to the lower clutch 11, the position where the point B (which is the tip of the pin 13 standing upright on the lower clutch 11) contacts the underside of the upper clutch 12, and the inclination of the two directions (one being widthwise and the other being normal to the line connecting the right and left sides of each clutch). The measurement of these parameters starts with setting three reference points on the face of the patient. As shown in FIG. 2, the three points are the right and left earholes H and the margo infraorbitalis S. The plane including these three points is used as the maxillary reference plane. A face-bow 17 is placed on this reference plane, and a shaft 18 connected perpendicularly to the face-bow 17 is fixed to the upper clutch 12. The lower end of the shaft 18 is secured to the sensor 14 for detecting light images in three orthogonal directions. The upper and lower clutches 11 and 12 are inserted into the patient's mouth and fastened to the teeth of the maxilla and mandible by plaster of Paris. An arm 19 is secured to the sensor 14 at a right angle with respect to the shaft 18. The arm 19 is connected to the upper clutch 12 through connecting rods 20 and 21 and two universal ball joints. The point light source A is similarly connected to the lower clutch 11 through an arm 24, connecting rods 22 and 23, and two universal ball joints. In order to simulate the mandibular movement, the mandibular is moved by contacting the pin 13 on the lower clutch 11 with the underside of the upper clutch 12, and the resulting displacement of the point light source A is detected by the sensor 14. However, the conventional system shown in FIG. 2 provides no means for making necessary corrections for the position and inclination of the upper and lower clutches 11, 12. Therefore, the dentist has to measure the two parameters with a scale and a protractor which are put on the lateral side of the patient's face.

Figure 3:
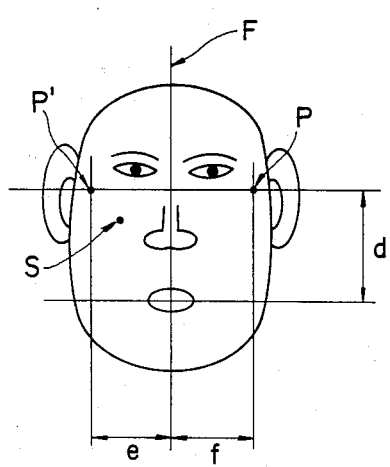
FIGS. 3 to 5 show diagrammatically how the maxillary reference plane of a face varies from person to person.
Figure 4:
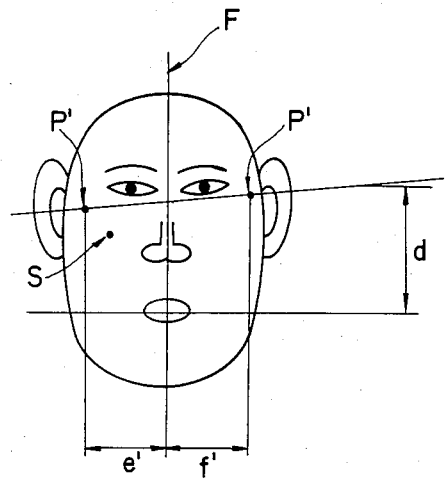
Figure 5:
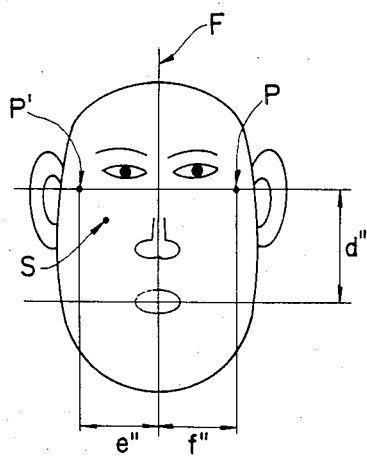

For the purpose of achieving a higher accuracy of occlusion, it is preferred to determine the maxillary reference plane, not on the basis of the margo infraorbitalis S and earholes H, but on the basis of the margo infraorbitalis S and the centric points of the right and left condyles P and P'. Three drawings of the patient's full face are shown in FIGS. 3 to 5, wherein P and P' indicate the condyles around which the mandible is moved, S is the margo infraorbitalis, and F is the median plane. As these figures show, the positional relationship of these points differs from one patient to another even if the condyles P and P' are used as the reference points. Needless to say, the position and posture of each clutch as measured in terms of the dimensions a and b (see FIG. 2) with a fixed scale formed by the face-bow 17 and the shaft 18 will also vary from one patient to another.

Figure 6:
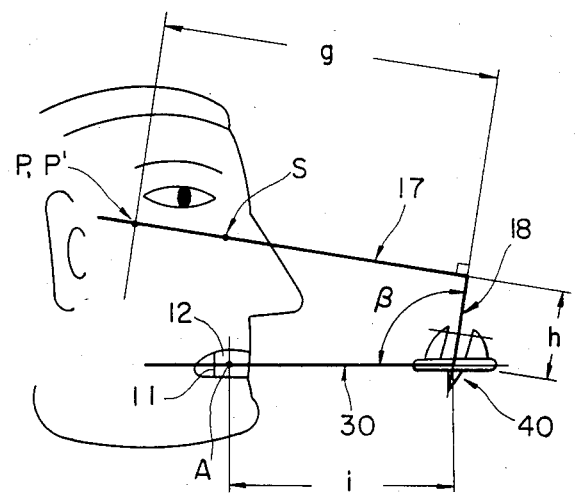
FIG. 6 illustrates the method of measuring various dimensions of a human face by the apparatus of the present invention.

FIG. 6 shows diagrammatically the method of determining the position and attitude of the upper and lower clutches 12, 11 using the apparatus of the present invention. As in the conventional technique, the maxillary reference plane connecting the condyles P, P' and the margo infraorbitalis S is combined with a shaft 18 perpendicular to that reference plane. However, according to the present invention, an arm 30 extending from the shaft 18 is directly coupled to the clutches 11 and 12 without universal ball joints and other intervening members. The attitude of each clutch (in the direction of pitch in FIG. 6, which is a side view of the human face) is measured as the angle $\beta$ by an attitude measuring device 40. Dimensions g and h are also variables (i is constant), but the method of the present invention ensures the simultaneous measurement of the position of the point A (i.e., the point light source).

Figure 7:
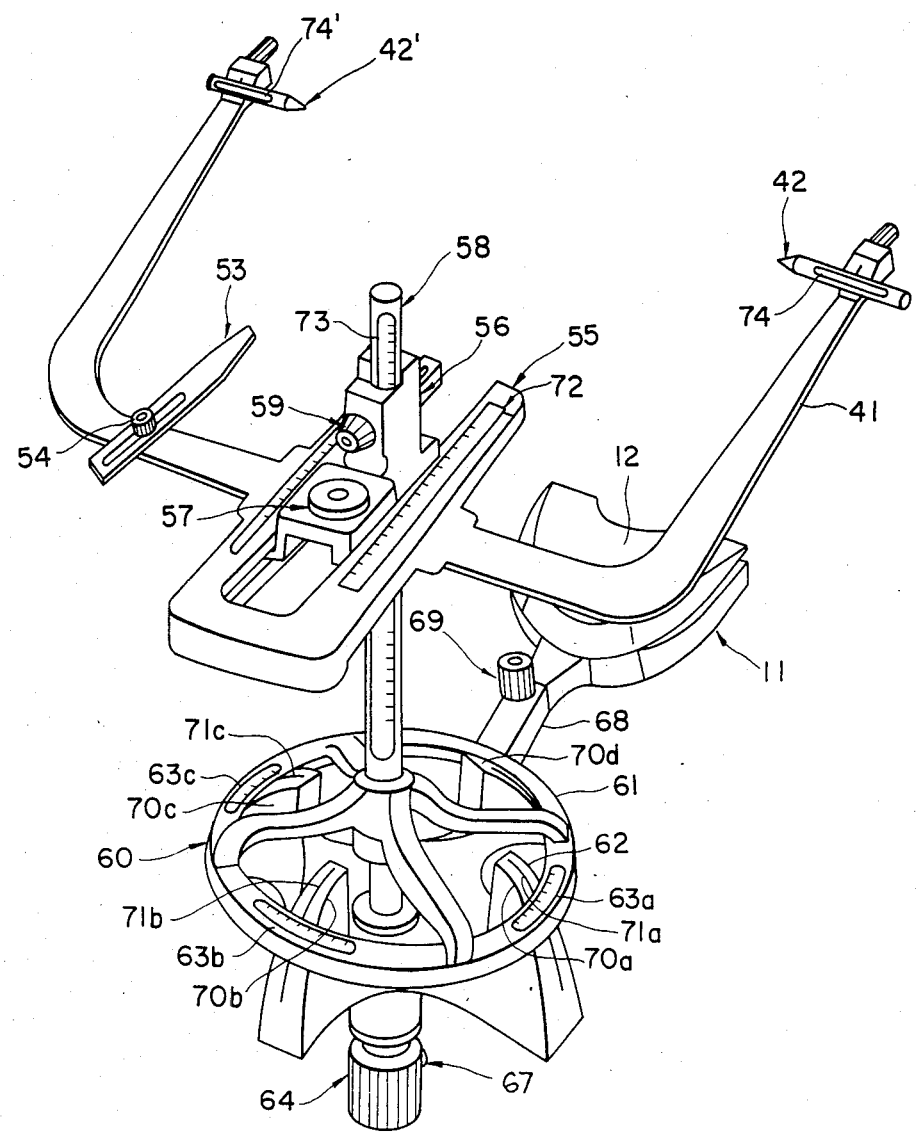
FIG. 7 is a perspective view of the apparatus of the present invention.

FIG. 7 is a general view of the apparatus of the present invention which is combined with upper and lower clutches. The apparatus has a face-bow 41 equipped with pins 42 and 42' that are to contact the patient's condyles P and P', and an occlusal pointer 53 which indicates the position of margo infraorbitalis S consisting of a lower clutch 11 and an upper clutch 12. The pins 42, 42' have scales 74, 74' marked thereon. The pin 42 is provided on the free end of one arm of the face-bow 41, and the pin 42' is provided on the free end of the other arm. Each pin 42, 42' is slidable along its axis. The two pin 42, 42' are preferably adjusted in such a manner that they project from the arms of the face-bow 41 by a substantially equal distance when they are brought into contact with the patient's face. Then, loosen a screw 54 on the occlusal pointer 53, adjust the occlusal pointer 52 so that it is directed to the patient's margo infraorbitalis S, and tighten the screw 54 to fix the occlusal pointer 53. These procedures complete the setting of the reference plane for the subsequent measurements.

The face-bow 41 is provided in the center with a mount 55 on which an attitude measuring sphere 60 is installed through a fixing block 56. The fixing block 56 is slidable along the length of the mount 55 and can be fixed at any point with a screw 57. A mounting shaft 58 is vertically movable through the fixing block 56 and can also be fixed at any point by a screw 59. The horizontal position of the mounting shaft 58 relative to the face-bow 41 can be read on a scale 72, and the vertical position of the mounting shaft 58 relative to the face-bow 41 can be read on a scale 73. On the lower end of the mounting shaft 58 is mounted the attitude measuring sphere 60 which consists of a ring 61 and an indicator 62 which reads certain values on corresponding calibrated scales 63a, 63b, and 63c marked on the ring 61.

Figure 9:
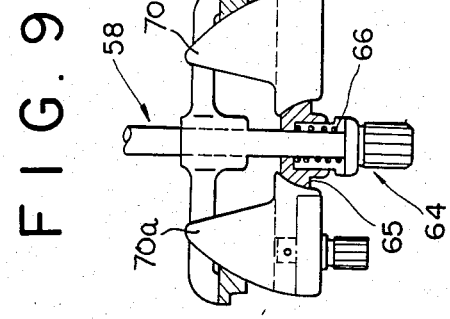
FIG. 9 is a cross section of the essential parts of FIG. 8.

The indicator 62 has four individually adjustable claws 70a through 70d that are urged into contact with the ring 61 by the spring-loaded holder 64. The mechanism of holder 64 is shown in FIG. 9, where a hemisphere 65 inscribed in the area defined by the claws 70a–70d of the indicator 62 is urged by a spring 66 the lower end of which contacts a pressure adjusting screw 67 threaded onto the mounting shaft 58 and housed within the hemisphere 65. The pressure given by the spring 66 can be varied by adjusting the pressure adjusting screw 67 (shown in FIG. 7). The indicator 62 is made integral with a joint 68 for achieving connection to the clutches 11 and 12 by a screw 69.

Figure 8:
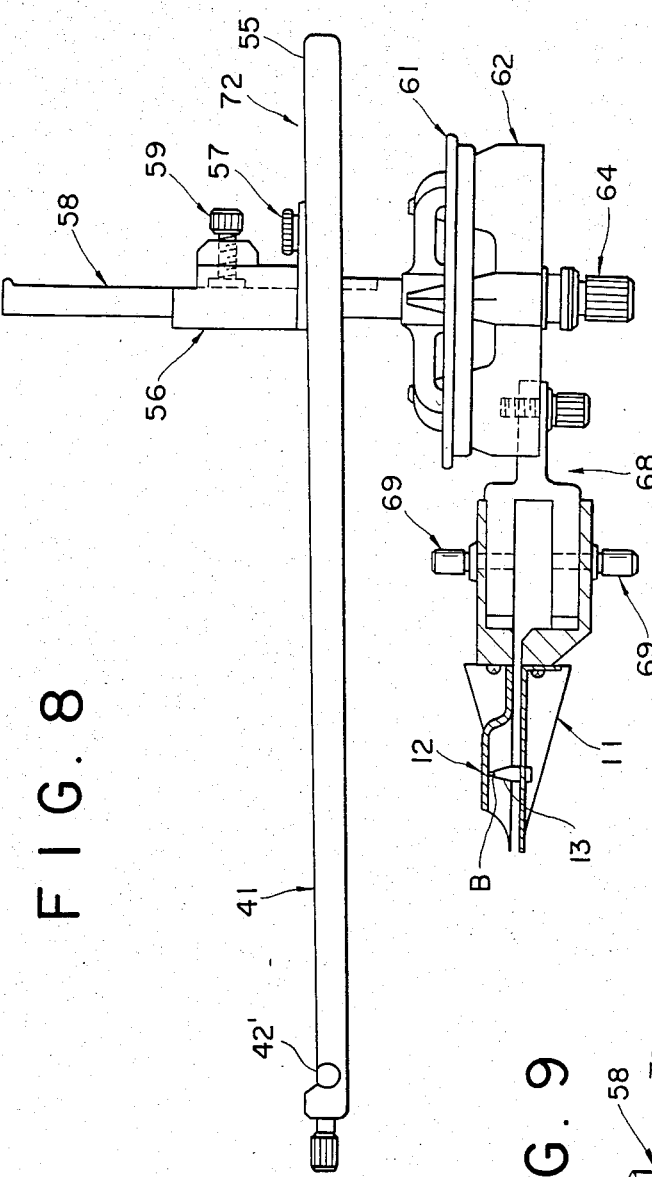
FIG. 8 is a side view of FIG. 7.

Details of the attitude measuring sphere are shown in FIGS. 8 and 9. The method of measuring the upper and lower clutches with this sphere proceeds as follows. In FIG. 8, the ring 61 is fixed to the mounting shaft 58. Below the ring 61, the indicator 62 is installed, and the spring-loaded holder 64 is inserted into the indicator 62. The four claws 70a, 70b, 70c, and 70d of the indicator 62 define part of the spherical plane and are held in contact with the ring 61. The claws 70a, 70b, and 70c are marked with lines of longitude 71a, 71b, and 71c that intersect three scales provided on the ring 61. The claws 70a–70b of the indicator 62 make face contact not only with the ring 61 but also with the holder 64. The two imaginary circles created by this face contact are concentric with each other. By tightening the screw 67 (FIG. 7), a sufficient torque is produced to give a desired upward bias to the claws 70a–70d on the indicator 62. As previously stated, the claws 70a–70d slide on an imaginary spherical surface.

Using the apparatus shown in FIG. 7, the three-dimensional position of the center of the sphere including claws 70a, 70b, 70c and 70d with respect to the maxillary reference coordinate system having as the origin the intersection of the median plane F with the axis connecting the condyles P and P' can be calculated from three parameters, i.e., (1) the distance between each condyle and the center of the mounting shaft 58, (2) the distance h between the horizontal reference plane defined by the face-bow 41 and the center of the indicator 62, and (3) the horizontal position calculated from the difference between the readings on the scales 74 and 74' marked on the pins 42 and 42'. The first two parameters can be determined by direct reading of the scales 72 and 73, respectively.

Figure 10:
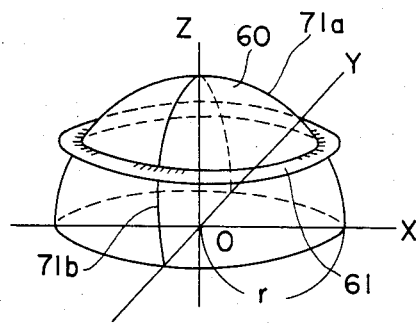
FIG. 10 illustrates the theory of measurement according to the present invention.
Figure 10:
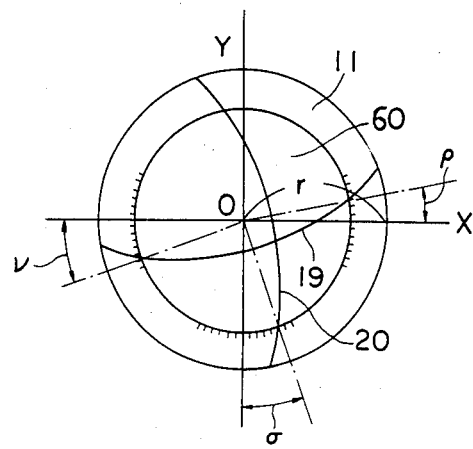
Figure 10:
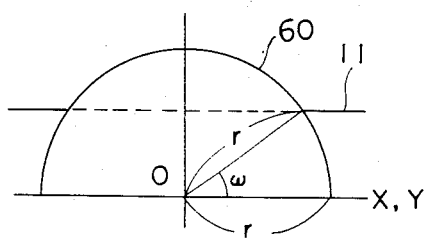
Figure 10:
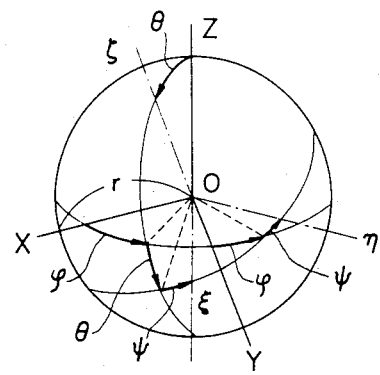

The three-dimensional attitude of the indicator 62 can be calculated from the positional relationship between the ring 61 and the indicator 62 that is determined on the basis of the calibrated readings of scales 63a, 63b, and 63c on the ring 61. FIGS. 10(a) to (d) illustrate the theory of calculating the necessary postural data from the readings of the scales 63a–63c on the ring 61. FIG. 10(a) is a perspective view of the attitude measuring sphere 60; FIG. 10(b) is a plan view of the attitude measure sphere 60; FIG. 10(c) is a side view of the attitude measure sphere 60; FIG. 10(d) is a schematic diagram for Euler's angles representing a three-dimensional attitude. In FIG. 10(a), the numeral 60 indicates part of the spherical surface defined by the claws 70a to 70d of the indicator 62. The four claws 70a–70d of the indicator 62 are marked with orthogonal lines of longitude 71a and 71b. In FIG. 10(a), these longitude lines are shown in their original positions, and in FIG. 10(b) they are shown in inclined positions. Suppose the readings of the three scales on the ring 61 are $\rho$, $\sigma$ and $\nu$. If the upper clutch 12 to which the indicator 62 is fixed is inclined by Euler's angles $\theta$, $\zeta$ and $\phi$ with respect to the maxillary reference coordinate system to which the ring 61 is fixed, analytical solid geometry shows that the following relations are established irrespective of the radius (r) of the attitude measuring sphere 60:

$$(\sin\psi\cos\phi + \cos\theta\cos\psi\sin\phi)\cos\rho - (\cos\psi\cos\phi - \cos\theta\sin\psi\sin\phi)\sin\rho - \sin\theta\sin\phi\tan\omega = 0$$

$$(\sin\psi\cos\phi + \cos\theta\cos\psi\sin\phi)\cos\nu - (\cos\psi\cos\phi - \cos\theta\sin\psi\sin\phi)\sin\nu + \sin\theta\sin\phi\tan\omega = 0$$

$$(\sin\psi\cos\phi - \cos\theta\cos\psi\cos\phi)\sin\sigma + (\cos\psi\sin\phi - \cos\theta\sin\psi\cos\phi)\cos\sigma + \sin\theta\cos\phi\tan\omega = 0$$

By solving these simultaneous equations with a computer, Euler's angles $\theta$, $\psi$ and $\phi$ can be calculated from the measurements of $\rho$, $\sigma$ and $\nu$. Given these Euler's angles, the fixed reference coordinate system X-Y-Z shown in FIG. 10(d) can be transformed to the $\xi$-$\eta$-$\zeta$ coordinate system by known formulae. If the positions of specific points in the $\xi$-$\eta$-$\zeta$ coordinate system as known, the positions of these points in the maxillary coordinate system having as the origin the center 0 of the attitude measuring sphere 60 can be calculated. Given the data on the three-dimensional position of the center 0 obtained by the readings of the scales on the face-bow 41, the positions of the respective points in the maxillary reference coordinate system having as the origin the intersection of the median plane F with the axis connecting the condyles P and P' can be calculated. In consequence, the three-dimensional position and attitude of the upper clutch 12 with respect to the maxillary reference plane can be calculated. At the same time, the three-dimensional position and attitude of the sensor 14, the three-dimensional position of the point light source A with respect to the maxillary reference plane, and the three-dimensional position of the point where the bearing pin 13 on the lower clutch 11 contacts the underside of the upper clutch 12 can also be calculated. In order to measure the mandibular movements, the pressure adjusting screw 67 (FIG. 7), the joint 68, as well as attitude measuring device 40 (FIG. 6) and the face-bow 41 connected to the joint 68 are removed, and instead, the sensor 14 and the point light source A are fixed to the upper clutch 12 and the lower clutch 11, respectively. In this case, the output data from the sensor 14 indicating the three-dimensional displacement can be used to calculate the movements of the mandible and other parts the positions and attitude of which are determined by the procedures described above.

As mentioned in the earlier part of this specification, the present inventors previously filed Japanese Patent Application (OPI) No. 116258/79 which claimed an "apparatus for the measurement of multi-dimensional movements" which includes a point light source A fixed to the front end of a lower clutch mounted on the patient's mandible and a sensor consisting of three units of one-dimensional light image detector fixed to the front end of an upper clutch mounted on the teeth of the maxilla. After "detecting the three-dimensional displacement of the light source on the front end of the mandible", the mandibular movement can be measured electronically by the "apparatus for measuring the mandibular movement" described in Japanese Patent Application (OPI) No. 163043/80 also filed by the present inventors or the "method and apparatus for measuring the mode of mandibular movement" described in Japanese Patent Application No. 80316/81 also filed by the present inventors. As will be apparent from the description in the previous pages, the apparatus of the present invention can be used with this electronic measurement of the mandibular movement for the purpose of simple and precise measurement of the three-dimensional position and attitude of the upper and lower clutches.

The apparatus of the present invention is generally applicable to the case where it is required to effect the simple and precise static measurement of the three-dimensional position and attitude of a rigid body with respect to the reference coordinate system. As is well known, the position and attitude of a rigid body has six degrees of freedom in a three-dimensional space, and they can be completely satisfied by the apparatus of the present invention. Therefore, the applicability of the concept of the present invention is not limited to the electronic measurement of mandibular movements in reconstructive dentistry, but it is generally applicable to the case where there is the need for measuring the three-dimensional position and attitude of a rigid body with respect to the reference coordinate system.

It is also to be understood that the foregoing description and the drawings and operational formulae given in connection with that description are for illustrative purposes only, and various modifications will be apparent to those skilled in the art.

What is claimed is:

1. An apparatus for measuring the three-dimensional position and attitude of upper and lower clutches mounted on a patient's teeth, said apparatus comprising:
   (a) a face-bow;
   (b) a pair of pins movably mounted on said face-bow in position to contact a patient's condyles;
   (c) an occlusal pointer movably mounted on said face-bow in position to indicate the position of the patient's margo infraorbitalis;
   (d) a mounting shaft mounted on said face-bow and extending vertically thereto, said mounting shaft being movable relative to said face-bow both toward and away from the patient's face and vertically up and down;
   (e) first means for locking said mounting shaft in a horizontal position relative to said face-bow;
   (f) second means for locking said mounting shaft in a vertical position relative to said face-bow;
   (g) an attitude measuring sphere mounted on the lower end of said mounting shaft, said attitude measuring sphere comprising:
      (i) a ring that is perpendicular to and coaxial with said mounting shaft;
      (ii) a plurality of calibrated scales marked on said ring;
      (iii) an indicator mounted on said mounting shaft for vertical movement relative thereto;
      (iv) a plurality of claws mounted on said indicator, each one of said plurality of claws having a part-spherical surface that makes surface contact with a corresponding part-spherical surface on said ring and having a line thereon that cooperates with a corresponding one of said plurality of calibrated scales marked on said ring; and
      (v) third means for biasing said plurality of claws into surface contact with said ring; and
   (h) fourth means for rigidly connecting upper and lower clutches mounted on the patient's teeth to said indicator.

2. Apparatus as recited in claim 1 wherein each one of said plurality of claws is individually radially movable relative to said indicator.

* * * * *